United States Patent
Liang (12) 
(10) Patent No.: US 8,582,105 B1
(45) Date of Patent: Nov. 12, 2013

(54) METHOD AND APPARATUS FOR LEAK DETECTION IN H2SE FURNACE

(75) Inventor: Haifan Liang, Fremont, CA (US)

(73) Assignee: Intermolecular, Inc., San Jose, CA (US)

( * ) Notice: Subject to any disclaimer, the term of this patent is extended or adjusted under 35 U.S.C. 154(b) by 51 days.

(21) Appl. No.: 13/523,606

(22) Filed: Jun. 14, 2012

(51) Int. Cl.
*G01N 21/00* (2006.01)

(52) U.S. Cl.
USPC .......................................... 356/437; 250/343

(58) Field of Classification Search
USPC .............. 356/432–440, 51; 73/40.7; 250/343, 250/338.5, 330
See application file for complete search history.

(56) References Cited

U.S. PATENT DOCUMENTS

| | | | | |
|---|---|---|---|---|
| 3,393,552 | A * | 7/1968 | Burgess | 73/40.7 |
| 3,549,882 | A * | 12/1970 | Barrington | 250/373 |
| 3,591,944 | A * | 7/1971 | Wilcox | 53/408 |
| 5,029,463 | A * | 7/1991 | Schvester et al. | 73/40.7 |
| 5,430,293 | A * | 7/1995 | Sato et al. | 250/330 |
| 5,633,454 | A * | 5/1997 | Abe et al. | 73/40 |
| 6,351,984 | B1 * | 3/2002 | Srinivasan | 73/40.7 |
| 2006/0203248 | A1 * | 9/2006 | Reichardt et al. | 356/437 |
| 2008/0192232 | A1 * | 8/2008 | Ninomiya et al. | 356/51 |
| 2010/0064777 | A1 * | 3/2010 | Howieson | 73/40.7 |

* cited by examiner

*Primary Examiner* — Hoa Pham (57) ABSTRACT

A method for detecting leaks during high temperature selenization of Cu—In—Ga metal precursor films comprises positioning a light source on one side of a transparent reaction chamber or aligned with a window in an opaque reaction chamber. The method further comprises positioning a detector opposite the light source and detecting an intensity of light from the light source. Leaks in the seals of the reaction chamber will result in the formation of an opaque film on the walls of the reaction chamber. A decrease in the intensity of light incident on the detector will indicate the presence of the leak. A second method comprises measuring the reflection of the light source off of the reaction chamber wall or a window in the reaction chamber. An change in the reflected light will indicate a leak in the seals of the reaction chamber.

16 Claims, 8 Drawing Sheets

METHOD AND APPARATUS FOR LEAK DETECTION IN H2SE FURNACE

FIELD OF THE INVENTION

The present invention relates generally to methods for selenizing and/or sulfurizing thin film solar cells at high temperatures. More specifically, methods of selenizing and/or sulfurizing copper indium gallium (sulfide) selenide (CIG(S)Se, or CIGS) solar cells.

BACKGROUND OF THE INVENTION

Solar cells are photovoltaic (PV) devices that convert light into electrical energy. Solar cells have been developed as dean, renewable energy sources to meet growing demand. Solar cells have been implemented in a wide number of commercial markets including residential rooftops, commercial rooftops, utility-scale PV projects, building integrated PV (BIPV), building applied PV (BAPV), PV in electronic devices, PV in clothing, etc. Currently, crystalline silicon solar cells (both single crystal and polycrystalline) are the dominant technologies in the market. Crystalline silicon (cSi) solar cells must use a thick substrate (>100 um) of silicon to absorb the sunlight since it has an indirect band gap. Also, the absorption coefficient is low for crystalline silicon because of the indirect band gap. The use of a thick substrate also means that the crystalline silicon solar cells must use high quality material to provide long minority carrier lifetimes to allow the carriers to diffuse to the p-n junction. Therefore, crystalline silicon solar cell technologies lead to increased costs. Thin film photovoltaic (TFPV) solar devices based on amorphous silicon (a-Si), CIGS, CdTe, CZTS, etc. provide an opportunity to increase the material utilization since only thin films (<10 um) are generally required. The thin film solar cells may be formed from amorphous, nanocrystalline, micro-crystalline, or mono-crystalline materials. TFPV devices may have a single device configuration (i.e. they are comprised of a single light conversion device) or they may have a tandem configuration wherein multiple TFPV devices are used to increase the absorption efficiency within different wavelength regions of the incident light spectrum.

TFPV devices provide an opportunity to reduce energy payback time, and reduce water usage for solar panel manufacturing. The absorption coefficient for CIGS is about $10^5$/cm. CIGS films have bandgaps in the range of 1.0 eV (CIS) to 1.65 eV (CGS) and are also efficient absorbers across the entire visible spectrum. Among the thin film solar technologies, CIGS has demonstrated the best lab cell efficiency (over 20%) and the best large area module efficiency (>15%).

A general class of PV absorber films of special interest is formed as multinary compounds from Groups IB-IIIA-VIA of the periodic table. Group IB includes Cu, Ag, and Au, Group IVA includes B. Al, Ga, hi, and TI. Group VIA includes O, S, Se, Te, and Po. Additionally, the IB-IIIA-VIA materials can be doped with dopants from Groups VIII, IIB, IVA, VA, and VHA of the periodic table. Group VII includes Fe, Ru, Os, Co, Rh, Ir, Ni, Pd, and Pt. Group IIB includes Zn, Cd, and Hg. Group IVA includes C, Si, Ge, Sn, and Pb. Group VA includes N, P, As, Sb, and Bi. Group VIIA includes F, Cl, Br, I, and At. Other potential absorber materials of interest include cuprous oxide, iron sulfide, etc.

TFPV devices can be fabricated at the cell level or the panel level, thus further decreasing the manufacturing costs. As used herein, the cell level is understood to mean an individual unit that can be combined with other units to form a module. The cells may be rigid or flexible. As used herein, the panel level is understood to mean a large TFPV structure that is not composed of smaller units. Generally, the panels are similar in size to the aforementioned modules. For economy of language, the phrase "TFPV device" will be understood to refer to either a solar cell or a panel without distinction. Furthermore, TFPV devices may be fabricated on inexpensive substrates such as glass, plastics, and thin sheets of metal. Examples of suitable substrates comprise float glass, low-iron glass, borosilicate glass, flexible glass, specialty glass for high temperature processing, stainless steel, carbon steel, aluminum, copper, polyimide, plastics, etc. Furthermore, the substrates may be processed in many configurations such as single substrate processing, multiple substrate batch processing, in-line continuous processing, roll-to-roll processing, etc.

The increasing demand for environmentally friendly, sustainable and renewable energy sources is driving the development of large area, thin film photovoltaic devices. With a long-term goal of providing a significant percentage of global energy demand, there is a concomitant need for Earth-abundant, high conversion efficiency materials for use in photovoltaic devices. A number of Earth abundant direct-bandgap semiconductor materials now seem to show evidence of the potential for both high efficiency and low cost in Very Large Scale (VLS) production (e.g. greater than 100 gigawatt (GW)), yet their development and characterization remains difficult because of the complexity of the materials systems involved.

The complexity of TFPV devices exploiting Earth abundant materials represents a daunting challenge in terms of the time-to-commercialization. That same complexity also suggests an enticing opportunity for breakthrough discoveries. A quaternary system such as CGS requires management of multiple kinetic pathways, thermodynamic phase equilibrium considerations, defect chemistries, and interfacial control. The vast phase-space to be managed includes process parameters, source material choices, compositions, and overall integration schemes. The complexity of the intrinsically-doped, self-compensating, multinary, polycrystalline, queue-time-sensitive, thin-film absorber (CIGS), and its interfaces to up-, and down-stream processing, combined with the lack of knowledge on a device level to address efficiency losses effectively, makes it a highly empirical material system. The performance of any thin-film, (opto-)electronically-active device is extremely sensitive to its interfaces. Interface engineering for electronically-active devices is highly empirical. Traditional R&D methods are ill-equipped to address such complexity, and the traditionally slow pace of R&D could limit any new material from reaching industrial relevance when having to compete with the incrementally improving performance of already established TFPV fabrication lines, and continuously decreasing panel prices for more traditional cSi PV technologies.

However, due to the complexity of the material, cell structure and manufacturing process, both the fundamental scientific understanding and large scale manufacturability are yet to be improved for CIGS TFPV devices. As the photovoltaic industry pushes to achieve grid parity, much faster and broader investigation is needed to explore the material, device, and process windows for higher efficiency and a lower cost of manufacturing process. Efficient methods for forming different types of CIGS TFPV devices that can be evaluated are necessary.

Typically, CIGS is formed by the selenization of Cu—In—Ga precursors that have been previously deposited. The selenization is typically performed in a batch furnace using $H_2Se$ gas as the source of Se. A problem encountered in this process is the presence of oxygen or water during the selenization step due to leaks in the seals of the reaction chamber. If oxygen or water is present while the H$_2$Se is flowing into the furnace, they will react to form elemental Se and/or selenium oxides and will have a negative impact on the selenization of the precursor film. Common sources of oxygen or water are leaks in the seals of the furnace. It is difficult to measure oxygen or water in an H$_2$Se environment due to the toxicity and corrosive nature of the H$_2$Se. Although oxygen sensors exist, they are costly and may not function due to the corrosive nature of the H$_2$Se in this application. Therefore, there is a need to develop systems and methods for the detection of leaks in a reaction chamber used for the selenization of CIG precursor films used in the formation of CIGS devices.

SUMMARY OF THE DISCLOSURE

In some embodiments of the present invention, a method for detecting leaks during high temperature selenization of Cu—In—Ga metal precursor films comprises positioning a light source on one side of a transparent reaction chamber or aligned with a window in an opaque reaction chamber. The method further comprises positioning a detector opposite the light source and detecting an intensity of light from the light source. Leaks in the seals of the reaction chamber will result in the formation of an opaque film on the walls of the reaction chamber. A decrease in the intensity of light incident on the detector will indicate the presence of the leak.

In some embodiments of the present invention, a method for detecting leaks during high temperature selenization of Cu—In—Ga metal precursor films comprises positioning a light source on one side of a transparent reaction chamber or aligned with a window in an opaque reaction chamber. The method further comprises positioning a detector aligned with the light source and detecting the reflection of light from the reaction chamber wall or window. Leaks in the seals of the reaction chamber will result in the formation of an opaque film on the walls of the reaction chamber and increase the reflected light intensity. An increase in the intensity of light incident on the detector will indicate the presence of the leak.

BRIEF DESCRIPTION OF THE DRAWINGS

To facilitate understanding, identical reference numerals have been used, where possible, to designate identical elements that are common to the figures. The drawings are not to scale and the relative dimensions of various elements in the drawings are depicted schematically and not necessarily to scale.

The techniques of the present invention can readily be understood by considering the following detailed description in conjunction with the accompanying drawings, in which:

FIGS. 5A and 8B illustrate schematic diagrams of leak detection using reflection.

DETAILED DESCRIPTION

A detailed description of one or more embodiments is provided below along with accompanying figures. The detailed description is provided in connection with such embodiments, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For the purpose of clarity, technical material that is known in the technical fields related to the embodiments has not been described in detail to avoid unnecessarily obscuring the description.

As used herein, "CIGS" will be understood to represent the entire range of related alloys denoted by Cu$_z$In$_{(1-x)}$Ga$_x$S$_{(2+w)(1-y)}$Se$_{(2+w)y}$, where $0.5 \leq z \leq 1.5$, $0 \leq x \leq 1$, $0 \leq y \leq 1$, $-0.25 \leq w \leq 0.5$ As used herein, "CZTS" will be understood to represent the entire range of related alloys denoted by Cu$_2$ZnSn(S$_y$Se$_{1-y}$)$_4$ where $0 \leq y \leq 1$. Similarly, as noted above, other IB-IIIA-VIA materials may be used as potential absorber layers. Also as mentioned previously, any of these materials may be further doped with a suitable dopant.

Figure 3:
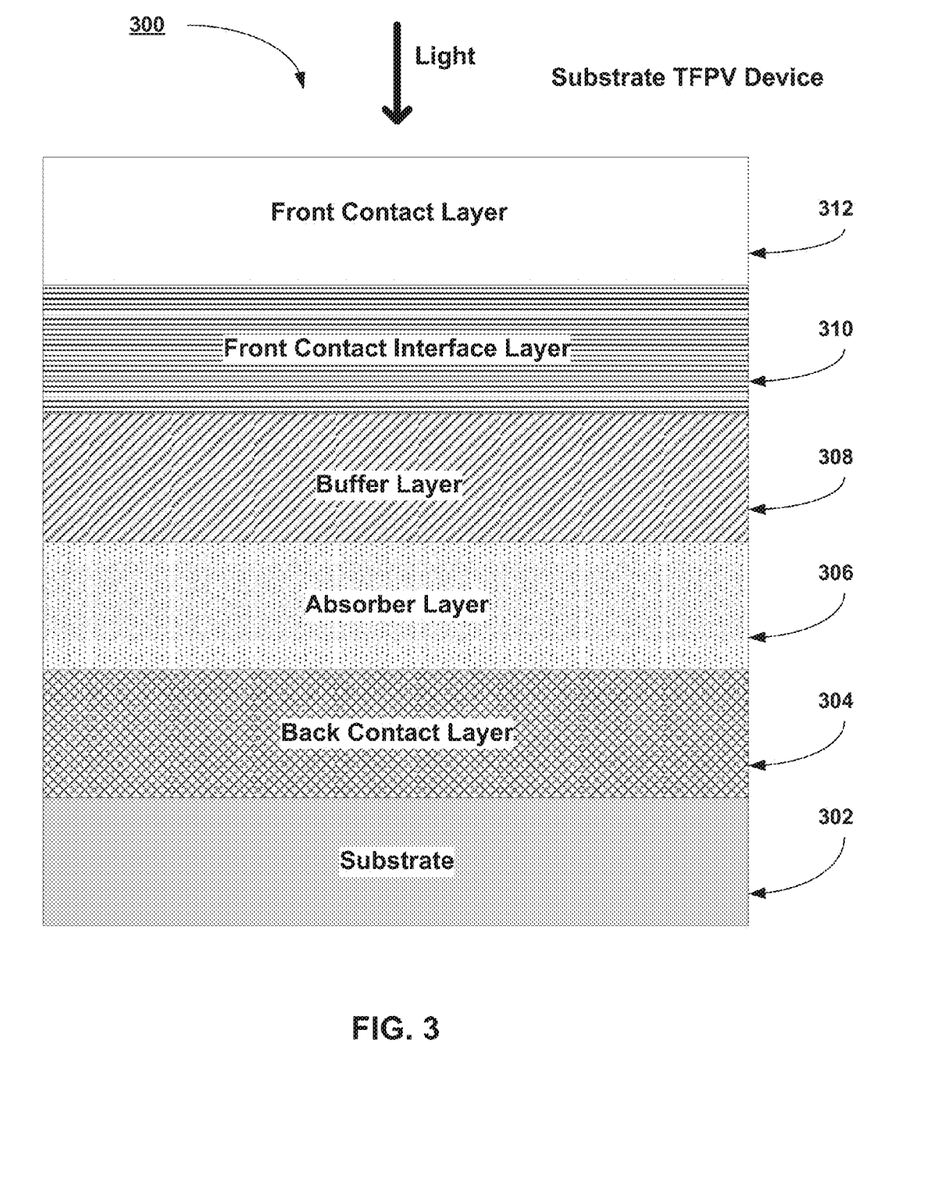
FIG. 3 illustrates a schematic diagram of a simple substrate TFPV stack according to an embodiment described herein.

In FIG. 3 below, a TFPV material stack is illustrated using a simple planar structure. Those skilled in the art will appreciate that the description and teachings to follow can be readily applied to any simple or complex TFPV solar cell morphology. The drawings are for illustrative purposes only and do not limit the application of the present invention.

The efficiency of TFPV devices depends on many properties of the absorber layer such as crystallinity, grain size, composition uniformity, density, defect concentration, doping level, surface roughness, etc. These properties may be influenced by the details of the process conditions under which the layer is formed or treated.

The manufacture of TFPV devices entails the integration and sequencing of many unit processing steps. As an example, TFPV manufacturing typically includes a series of processing steps such as cleaning, surface preparation, deposition, patterning, etching, thermal annealing, and other related unit processing steps. The precise sequencing and integration of the unit processing steps enables the formation of functional devices meeting desired performance metrics such as efficiency, power production, and reliability.

As part of the discovery, optimization and qualification of each unit process, it is desirable to be able to i) test different materials, ii) test different processing conditions within each unit process module, iii) test different sequencing and integration of processing modules within an integrated processing tool, iv) test different sequencing of processing tools in executing different process sequence integration flows, and combinations thereof in the manufacture of devices such as TFPV devices. In particular, there is a need to be able to test i) more than one material, ii) more than one processing condition, iii) more than one sequence of processing conditions, iv) more than one process sequence integration flow, and combinations thereof, collectively known as "combinatorial process sequence integration", on a single substrate without the need of consuming the equivalent number of monolithic substrates per material(s), processing condition(s), sequence(s) of processing conditions, sequence(s) of processes, and combinations thereof. This can greatly improve both the speed and reduce the costs associated with the discovery, implementation, optimization, and qualification of material(s), process(es), and process integration sequence(s) required for manufacturing.

Systems and methods for High Productivity Combinatorial (HPC) processing are described in U.S. Pat. No. 7,544,574 filed on Feb. 10, 2006, U.S. Pat. No. 7,824,935 filed on Jul. 2, 2008, U.S. Pat. No. 7,871,928 filed on May 4, 2009, U.S. Pat. No. 7,902,063 filed on Feb. 10, 2006, and U.S. Pat. No. 7,947,531 filed on Aug. 28, 2009 which are all herein incorporated by reference. Systems and methods for HPC processing are further described in U.S. patent application Ser. No. 11/352,077 filed on Feb. 10, 2006, claiming priority from Oct. 15, 2005, U.S. patent application Ser. No. 11/419,174 filed on May 18, 2006, claiming priority from Oct. 15, 2005, U.S. patent application Ser. No. 11/674,132 filed on Feb. 12, 2007, claiming priority from Oct. 15, 2005, and U.S. patent application Ser. No. 11/674,137 filed on Feb. 12, 2007, claiming priority from Oct. 15, 2005 which are all herein incorporated by reference.

HPC processing techniques have been successfully adapted to wet chemical processing such as etching, texturing, polishing, cleaning, etc. HPC processing techniques have also been successfully adapted to deposition processes such as sputtering, atomic layer deposition (ALD), and chemical vapor deposition (CVD).

Figure 1:
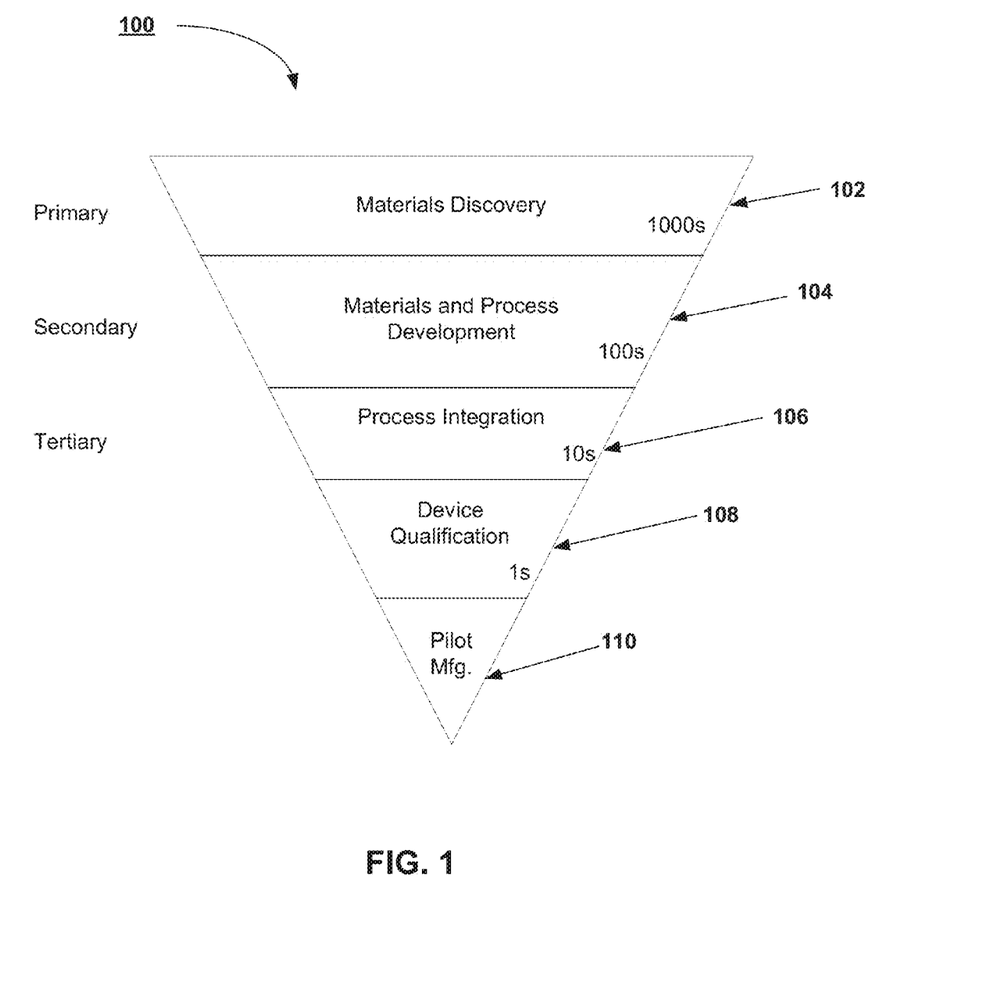
FIG. 1 is a schematic diagram for implementing combinatorial processing and evaluation.

FIG. 1 illustrates a schematic diagram, 100, for implementing combinatorial processing and evaluation using primary, secondary, and tertiary screening. The schematic diagram, 100, illustrates that the relative number of combinatorial processes run with a group of substrates decreases as certain materials and/or processes are selected. Generally, combinatorial processing includes performing a large number of processes during a primary screen, selecting promising candidates from those processes, performing the selected processing during a secondary screen, selecting promising candidates from the secondary screen for a tertiary screen, and so on. In addition, feedback from later stages to earlier stages can be used to refine the success criteria and provide better screening results.

For example, thousands of materials are evaluated during a materials discovery stage, 102. Materials discovery stage, 102, is also known as a primary screening stage performed using primary screening techniques. Primary screening techniques may include dividing substrates into coupons and depositing materials using varied processes. The materials are then evaluated, and promising candidates are advanced to the secondary screen, or materials and process development stage, 104. Evaluation of the materials is performed using metrology tools such as electronic testers and imaging tools (i.e., microscopes).

The materials and process development stage, 104, may evaluate hundreds of materials (i.e., a magnitude smaller than the primary stage) and may focus on the processes used to deposit or develop those materials. Promising materials and processes are again selected, and advanced to the tertiary screen or process integration stage, 106, where tens of materials and/or processes and combinations are evaluated. The tertiary screen or process integration stage, 106, may focus on integrating the selected processes and materials with other processes and materials.

The most promising materials and processes from the tertiary screen are advanced to device qualification, 108. In device qualification, the materials and processes selected are evaluated for high volume manufacturing, which normally is conducted on full substrates within production tools, but need not be conducted in such a manner. The results are evaluated to determine the efficacy of the selected materials and processes. If successful, the use of the screened materials and processes can proceed to pilot manufacturing, 110.

The schematic diagram, 100, is an example of various techniques that may be used to evaluate and select materials and processes for the development of new materials and processes. The descriptions of primary, secondary, etc. screening and the various stages, 102-110, are arbitrary and the stages may overlap, occur out of sequence, be described and be performed in many other ways.

This application benefits from High Productivity Combinatorial (HPC) techniques described in U.S. patent application Ser. No. 11/674,137 filed on Feb. 12, 2007 which is hereby incorporated for reference in its entirety. Portions of the '137 application have been reproduced below to enhance the understanding of the present invention. The embodiments described herein enable the application of combinatorial techniques to process sequence integration in order to arrive at a globally optimal sequence of TFPV manufacturing operations by considering interaction effects between the unit manufacturing operations, the process conditions used to effect such unit manufacturing operations, hardware details used during the processing, as well as materials characteristics of components utilized within the unit manufacturing operations. Rather than only considering a series of local optimums, i.e., where the best conditions and materials for each manufacturing unit operation is considered in isolation, the embodiments described below consider interactions effects introduced due to the multitude of processing operations that are performed and the order in which such multitude of processing operations are performed when fabricating a TFPV device. A global optimum sequence order is therefore derived and as part of this derivation, the unit processes, unit process parameters and materials used in the unit process operations of the optimum sequence order are also considered.

The embodiments described further analyze a portion or sub-set of the overall process sequence used to manufacture a TFPV device. Once the subset of the process sequence is identified for analysis, combinatorial process sequence integration testing is performed to optimize the materials, unit processes, hardware details, and process sequence used to build that portion of the device or structure. During the processing of some embodiments described herein, structures are formed on the processed substrate that are equivalent to the structures formed during actual production of the TFPV device. For example, such structures may include, but would not be limited to, contact layers, buffer layers, absorber layers, or any other series of layers or unit processes that create an intermediate structure found on TFPV devices. While the combinatorial processing varies certain materials, unit processes, hardware details, or process sequences, the composition or thickness of the layers or structures or the action of the unit process, such as cleaning, surface preparation, deposition, surface treatment, etc. is substantially uniform through each discrete region. Furthermore, while different materials or unit processes may be used for corresponding layers or steps in the formation of a structure in different regions of the substrate during the combinatorial processing, the application of each layer or use of a given unit process is substantially consistent or uniform throughout the different regions in which it is intentionally applied. Thus, the processing is uniform within a region (inter-region uniformity) and between regions (intra-region uniformity), as desired. It should be noted that the process can be varied between regions, for example, where a thickness of a layer is varied or a material may be varied between the regions, etc., as desired by the design of the experiment.

The result is a series of regions on the substrate that contain structures or unit process sequences that have been uniformly applied within that region and, as applicable, across different regions. This process uniformity allows comparison of the properties within and across the different regions such that the variations in test results are due to the varied parameter (e.g., materials, unit processes, unit process parameters, hardware details, or process sequences) and not the lack of process uniformity. In the embodiments described herein, the positions of the discrete regions on the substrate can be defined as needed, but are preferably systematized for ease of tooling and design of experimentation. In addition, the number, variants and location of structures within each region are designed to enable valid statistical analysis of the test results within each region and across regions to be performed.

Figure 2:
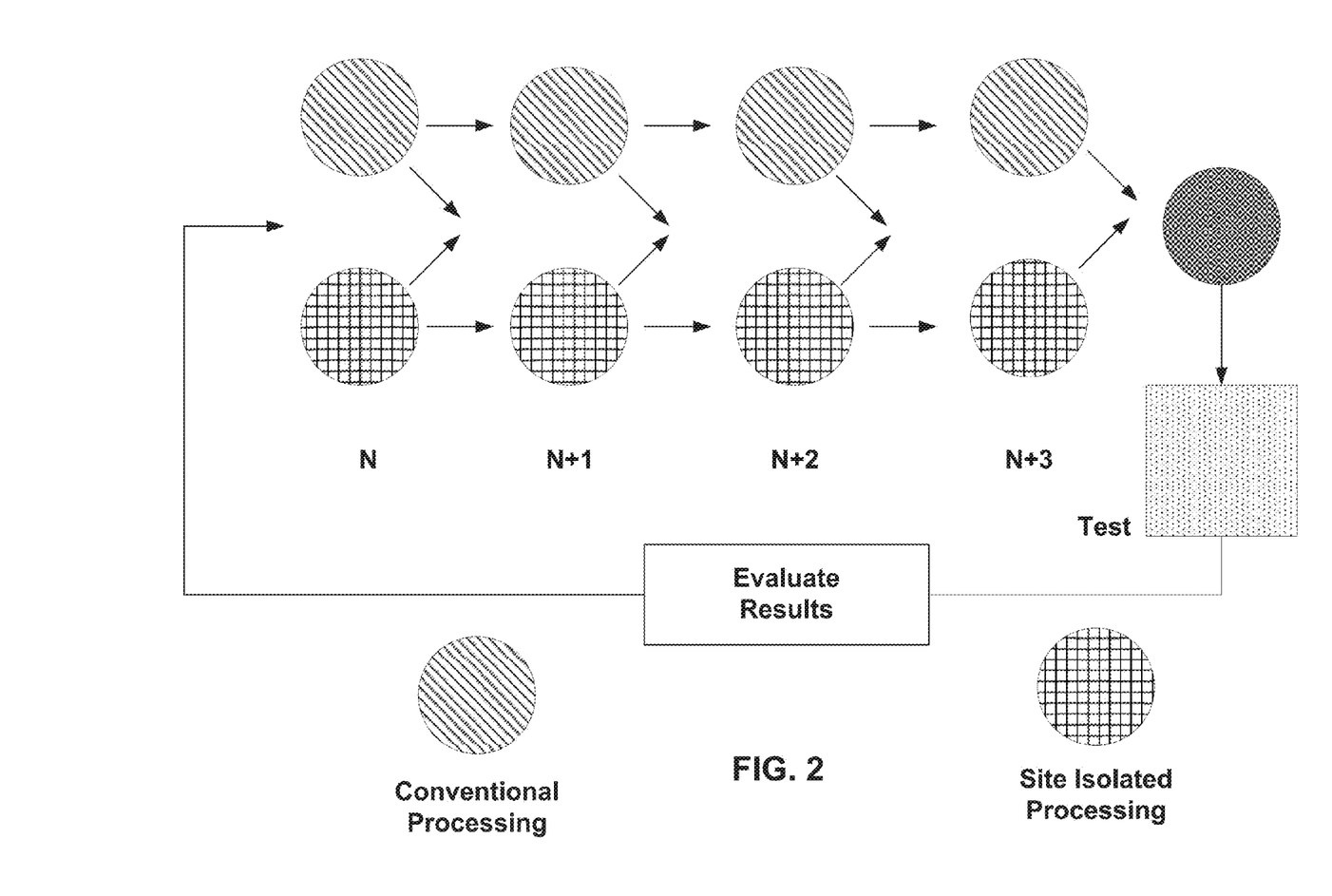
FIG. 2 is a schematic diagram for illustrating various process sequences using combinatorial processing and evaluation.

FIG. 2 is a simplified schematic diagram illustrating a general methodology for combinatorial process sequence integration that includes site isolated processing and/or conventional processing in accordance with one embodiment of the invention. In one embodiment, the substrate is initially processed using conventional process N. In one exemplary embodiment, the substrate is then processed using site isolated process N+1. During site isolated processing, an HPC module may be used, such as the HPC module described in U.S. patent application Ser. No. 11/352,077 filed on Feb. 10, 2006. The substrate can then be processed using site isolated process N+2, and thereafter processed using conventional process N+3. Testing is performed and the results are evaluated. The testing can include physical, chemical, acoustic, magnetic, electrical, optical, etc. tests. From this evaluation, a particular process from the various site isolated processes (e.g. from steps N+1 and N+2) may be selected and fixed so that additional combinatorial process sequence integration may be performed using site isolated processing for either process N or N+3. For example, a next process sequence can include processing the substrate using site isolated process N, conventional processing for processes N+1, N+2, and N+3, with testing performed thereafter.

It should be appreciated that various other combinations of conventional and combinatorial processes can be included in the processing sequence with regard to FIG. 2. That is, the combinatorial process sequence integration can be applied to any desired segments and/or portions of an overall process flow. Characterization, including physical, chemical, acoustic, magnetic, electrical, optical, etc. testing, can be performed after each process operation, and/or series of process operations within the process flow as desired. The feedback provided by the testing is used to select certain materials, processes, process conditions, and process sequences and eliminate others. Furthermore, the above flows can be applied to entire monolithic substrates, or portions of monolithic substrates such as coupons.

Under combinatorial processing operations the processing conditions at different regions can be controlled independently. Consequently, process material amounts, reactant species, processing temperatures, processing times, processing pressures, processing flow rates, processing powers, processing reagent compositions, the rates at which the reactions are quenched, deposition order of process materials, process sequence steps, hardware details, etc., can be varied from region to region on the substrate. Thus, for example, when exploring materials, a processing material delivered to a first and second region can be the same or different. If the processing material delivered to the first region is the same as the processing material delivered to the second region, this processing material can be offered to the first and second regions on the substrate at different concentrations. In addition, the material can be deposited under different processing parameters. Parameters which can be varied include, but are not limited to, process material amounts, reactant species, processing temperatures, processing times, processing pressures, processing flow rates, processing powers, processing reagent compositions, the rates at which the reactions are quenched, atmospheres in which the processes are conducted, an order in which materials are deposited, hardware details of the gas distribution assembly, etc. It should be appreciated that these process parameters are exemplary and no meant to be an exhaustive list as other process parameters commonly used in TFPV manufacturing may be varied.

As mentioned above, within a region, the process conditions are substantially uniform, in contrast to gradient processing techniques which rely on the inherent non-uniformity of the material deposition. That is, the embodiments, described herein locally perform the processing in a conventional manner, e.g., substantially consistent and substantially uniform, while globally over the substrate, the materials, processes, and process sequences may vary. Thus, the testing will find optimums without interference from process variation differences between processes that are meant to be the same. It should be appreciated that a region may be adjacent to another region in one embodiment or the regions may be isolated and, therefore, non-overlapping. When the regions are adjacent, there may be a slight overlap wherein the materials or precise process interactions are not known, however, a portion of the regions, normally at least 50% or more of the area, is uniform and all testing occurs within that region. Further, the potential overlap is only allowed with material of processes that will not adversely affect the result of the tests. Both types of regions are referred to herein as regions or discrete regions.

FIG. 3 illustrates a schematic diagram of a simple TFPV device stack in the substrate configuration consistent with some embodiments of the present invention. The convention will be used wherein light is assumed to be incident upon the top of the material stack in the substrate configuration as illustrated. This generic diagram would be typical of a CIGS TFPV device in a substrate configuration. A back contact layer, 304, is formed on a substrate, 302. Examples of suitable substrates comprise float glass, low-iron glass, borosilicate glass, flexible glass, specialty glass for high temperature processing, stainless steel, carbon steel, aluminum, copper, titanium, molybdenum, polyimide, plastics, cladded metal foils, etc. Furthermore, the substrates may be processed in many configurations such as single substrate processing, multiple substrate batch processing, in-line continuous processing, roll-to-roll processing, etc. As used herein, the phrase "back contact" will be understood to be the primary current conductor layer situated between the substrate and the absorber layer in a substrate configuration TFPV device. An example of a common back contact layer material is Mo for CIGS. The back contact layer may be formed by any number of deposition technologies. Examples of suitable deposition technologies comprise PVD (sputtering), evaporation, chemical vapor deposition (CVD), atomic layer deposition (ALD), plating, etc. The thickness of the back contact layer is typically between about 0.3 um and about 1.0 um. The back contact layer has a number of requirements such as high conductivity, good ohmic contact to the absorber layer, ease of bonding to tabs for external connectivity, ease of scribing or other removal, good thermo-mechanical stability, and chemical resistance during subsequent processing, among others.

Optionally, a diffusion barrier layer (not shown) may be formed between the substrate and the back contact layer. When implemented, the diffusion barrier layer stops the diffusion of impurities from the substrate into the back contact layer, or alternatively, stops the diffusion and reaction of the back contact material into the substrate. Examples of common diffusion barrier layers comprise chromium, vanadium, tungsten, nitrides such as tantalum nitride, tungsten nitride, titanium nitride, silicon nitride, zirconium nitride, hafnium nitride, oxy-nitrides such as tantalum oxy-nitride, tungsten oxy-nitride, titanium oxy-nitride, silicon oxy-nitride, zirconium oxy-nitride, hafnium oxy-nitride, oxides such as aluminum oxide, silicon oxide, carbides such as silicon carbide, binary and/or multinary compounds of tungsten, titanium, molybdenum, chromium, vanadium, tantalum, hafnium, zirconium, and/or niobium with/without the inclusion of nitrogen and/or oxygen. The diffusion barrier layer may be formed from any well known technique such as sputtering, CVD, evaporation, wet methods such as printing or spraying of inks, screen printing, inkjet printing, slot die coating, gravure printing, wet chemical depositions, or from sol-gel methods such as the coating, drying, and firing of polysilazanes.

A p-type absorber layer, 306, of CGS (or other IB-IIIA-VIA material) is then deposited on top of the back contact layer. The absorber layer may be formed using a variety of techniques such as PVD (sputtering), co-evaporation, in-line evaporation, plating, printing or spraying of inks, screen printing, inkjet printing, slot die coating, gravure printing, wet chemical depositions, CVD, etc. Advantageously, the absorber layer is deficient in Cu. Advantageously, the Cu concentration is between about 0.8 and 1.0 wherein the Cu concentration is calculated as Cu=(Cu/(In+Ga)). The Cu deficiency may be controlled by managing the deposition conditions. Advantageously, the Ga concentration is between about 0.2 and 0.4 wherein the Ga concentration is calculated as Ga=(Ga/(In+Ga)). Advantageously, a small amount of Na is contained in the absorber layer. The Na may be added by out-diffusion from the SLG substrate or may be purposely added in the form of $Na_2Se$ or another sodium source, prior, during, or after the deposition of the absorber layer. Typically, the absorber layer undergoes a selenization process after formation to convert the CIG precursor film into a high-quality CIGS semiconductor film. The selenization process involves the exposure of the CIG precursor layer to a Se-containing gas comprising at least one of $H_2Se$, Se vapor, or diethylselenide (DESe) at temperatures most typically between about 300 C and 700 C. It should be noted that the precursor to CIGS might already contain a chalcogen source (e.g. Se), either as a separate layer, or incorporated into the bulk of the precursor layer. The precursor film can be a stack of layers, or one layer. The precursor layer can be dense, or porous. The precursor film typically contains Cu, In, and Ga. The precursor layer is most commonly deposited by sputtering from e.g. binary copper-gallium and indium sputter targets. Nevertheless, plating and printing to deposit the metal precursor film containing Cu, In, and/or Ga are used as well. During the selenization process, a layer of $Mo(S)Se_2$ (not shown) forms at the back contact/absorber layer interface and forms a good ohmic contact between the two layers. The thickness of the absorber layer is typically between about 1.0 um and about 3.0 um. The performance of the absorber layer is sensitive to materials properties such as crystallinity, grain size, surface roughness, composition, defect concentration, etc. as well as processing parameters such as temperature, deposition rate, thermal treatments, etc.

An n-type buffer layer, 308, is then deposited on top of the absorber layer. Examples of suitable n-type buffer layers comprise CdS, ZnS, $In_2S_3$, $In_2(S,Se)_3$, CdZnS, ZnO, Zn(O, S), (Zn,Mg)O, etc. CdS is the material most often used as the n-type buffer layer in CIGS TFPV devices. The buffer layer may be deposited using chemical bath deposition (CBD), chemical surface deposition (CSD), PVD (sputtering), printing, plating, ALD, Ion-Layer-Gas-Reaction (ILGAR), or evaporation. The thickness of the buffer layer is typically between about 30 nm and about 100 nm. The performance of the buffer layer is sensitive to materials properties such as crystallinity, grain size, surface roughness, composition, defect concentration, etc. as well as processing parameters such as temperature, deposition rate, thermal treatments, etc.

Optionally, an intrinsic ZnO (iZnO) layer, 310, is then formed on top of the buffer layer. The iZnO layer is a high resistivity material and forms part of the transparent conductive oxide (TOO) stack that serves as part of the front contact structure. The TOO stack is formed from transparent conductive metal oxide materials and collects charge across the face of the TFPV solar cell and conducts the charge to tabs used to connect the device to external loads. The iZnO layer makes the TFPV solar cell less sensitive to lateral non-uniformities caused by differences in composition or defect concentration in the absorber and/or buffer layers. The iZnO layer is typically between about 0 nm and 150 nm in thickness. The iZnO layer is typically formed using a (reactive) PVD (sputtering) technique or CVD technique, but can be deposited by plating or printing as well. A low resistivity top TOO layer, 312, (examples include Al:ZnO (AZO), InSnO (ITO), InZnO, B:ZnO, Ga:ZnO, F:ZnO, $F:SnO_2$, etc.) is formed on top of the iZnO layer. The top TOO layer is typically between about 0.25 um and 1.0 um in thickness. The top TOO layer is typically formed using a (reactive) PVD technique or OVD technique. Optionally, the transparent top electrode can be printed or wet-coated from nano-wires, carbon nanotubes, and the like.

Figure 4:
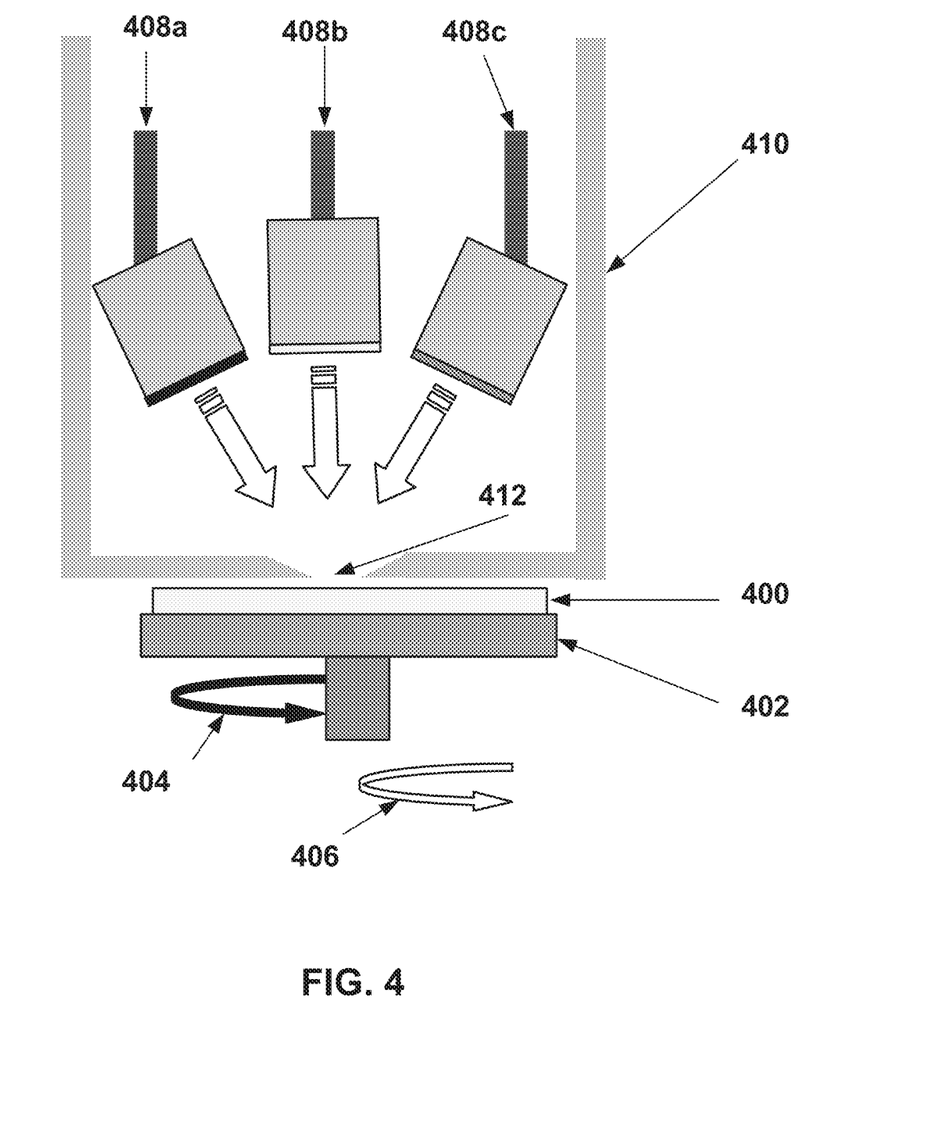
FIG. 4 illustrates a schematic diagram of a combinatorial PVD system according to an embodiment described herein.

FIG. 4 illustrates a schematic diagram of a combinatorial PVD system according to some embodiments described herein. Details of the combinatorial PVD system are described in U.S. patent application Ser. No. 12/027,980 filed on Feb. 7, 2008 and claiming priority to Sep. 5, 2007, and U.S. patent application Ser. No. 12/028,643 filed on Feb. 8, 2008 and claiming priority to Sep. 5, 2007. Substrate, 400, is held on substrate support, 402. Substrate support, 402, has two axes of rotation, 404 and 406. The two axes of rotation are not aligned. This feature allows different regions of the substrate to be accessed for processing in a site isolated manner. The substrate support may be moved in a vertical direction to alter the spacing between the PVD targets and the substrate. The combinatorial PVD system comprises multiple PVD assemblies configured within a PVD chamber (not shown). In FIG. 4, three PVD assemblies are shown, 408a-408c. Those skilled in the art will appreciate that any number of PVD assemblies may be used, limited only by the size of the chamber and the size of the PVD assemblies. Typically, four PVD assemblies are contained within the chamber. Advantageously, the multiple PVD assemblies contain different target materials to allow a wide range of material and alloys compositions to be investigated. Additionally, the combinatorial PVD system will typically include the capability for reactive sputtering in reactive gases such as $O_2$, $NH_3$, $N_2$, etc. The PVD assemblies may be moved in a vertical direction to alter the spacing between the PVD targets and the substrate and may be tilted to alter the angle of incidence of the sputtered material arriving at the substrate surface. The combinatorial PVD system further comprises a process kit shield assembly, 410. The process kit shield assembly includes an aperture, 412, used to define isolated regions on the surface of the substrate. The portion of the process kit shield assembly that includes the aperture may have both rotational and translational capabilities. The combination of the substrate support movement, PVD assembly movement, and process kit shield assembly aperture movement allows multiple regions of the substrate to be processed in a site isolated manner wherein each site can be processed without interference from adjacent regions. Advantageously, the process parameters among the multiple site isolated regions can be varied in a combinatorial manner.

Figure 5:
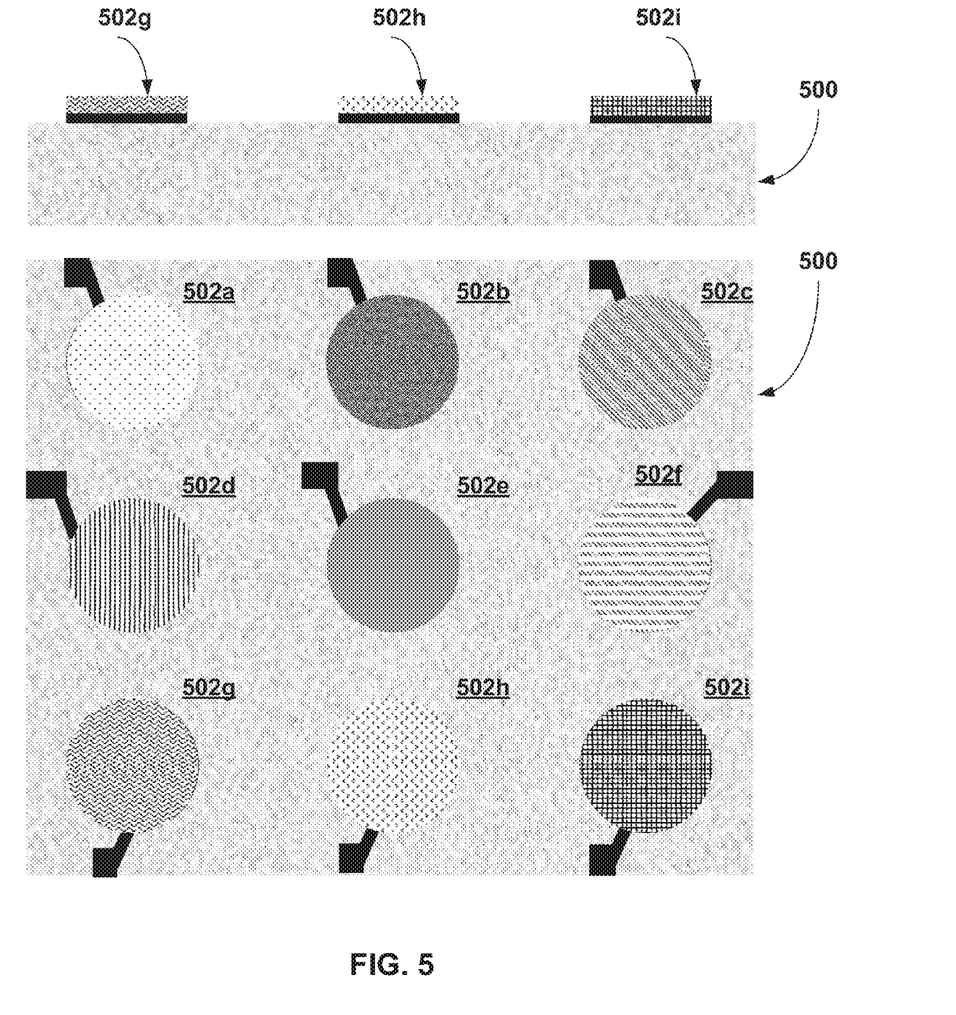
FIG. 5 illustrates a schematic diagram of a substrate that has been processed in a combinatorial manner.

FIG. 5 illustrates a schematic diagram of a substrate that has been processed in a combinatorial manner to form isolated regions on the substrate. Although the substrate in FIG. 5 is illustrated as being a generally square shape, those skilled in the art will understand that the substrate may be any useful shape such as round, rectangular, etc. FIG. 5 illustrates a substrate, 500, with nine site isolated regions, 502a-502i, illustrated thereon. The lower portion of FIG. 5 illustrates a top down view while the upper portion of FIG. 5 illustrates a cross-sectional view taken through the three site isolated regions, 502g-502i. The shading of the nine site isolated regions illustrates that the process parameters used to process these regions have been varied in a combinatorial manner. The substrate may then be processed through a next step that may be conventional or may also be a combinatorial step as discussed earlier with respect to FIG. 2.

It is desirable to optimize the selenization of the metal precursors by increasing the reaction temperature. At temperatures above about 550 C, In agglomeration competes against selenization. When In agglomeration is preferred over selenization, In particulates segregate from the metal precursor and form separate binary phases. The resulting films have a sporty and blister-like visual appearance. X-ray diffraction (XRD) spectra on these films show InSe (004) and (006) peaks besides the ternary chalcopyrite phases. There is no photo-luminescence (PL) intensity on these films and device results are poor. To solve this problem, an intermediate, lower temperature selenization step at between about 350 C and about 450 C is introduced to partially selenize the precursor before complete selenization at higher temperatures. The additional step secured the indium in a selenized state to prevent agglomeration. This eliminated the problem of binary phase formation in the final selenization step.

Another problem typically encountered during selenization is the difficulty to control the degree of selenization at higher reaction temperatures. The selenization reaction of GIGS occurs at temperatures above about 350 to about 450 C. In a batch furnace, the ramp rates are generally limited to about 10 C/min by hardware. When the maximum reaction temperature is increased, both the reaction rate and the reaction time are increased, including the period of time for heating up and cooling down. When the furnace temperature is increased to 600 C, delamination at the Mo/GIGS interface is observed due to over-selenization and formation of a thick $MoSe_2$ layer. In some embodiments of the present invention, a fast gas exchange step is introduced at the high temperature step to replace $H_2Se$ in the furnace with an inert gas such as Ar, $N_2$, etc. to stop further selenization. This resolves the delamination problem due to over-selenization by limiting the formation of the $MoSe_2$ layer. Details of the fast gas exchange process are described in U.S. patent application Ser. No. 13/283,225 entitled "Method of Fabricating CIGS by Selenization at High Temperature" filed on Oct. 27, 2011 and is herein incorporated by reference.

Figure 6:
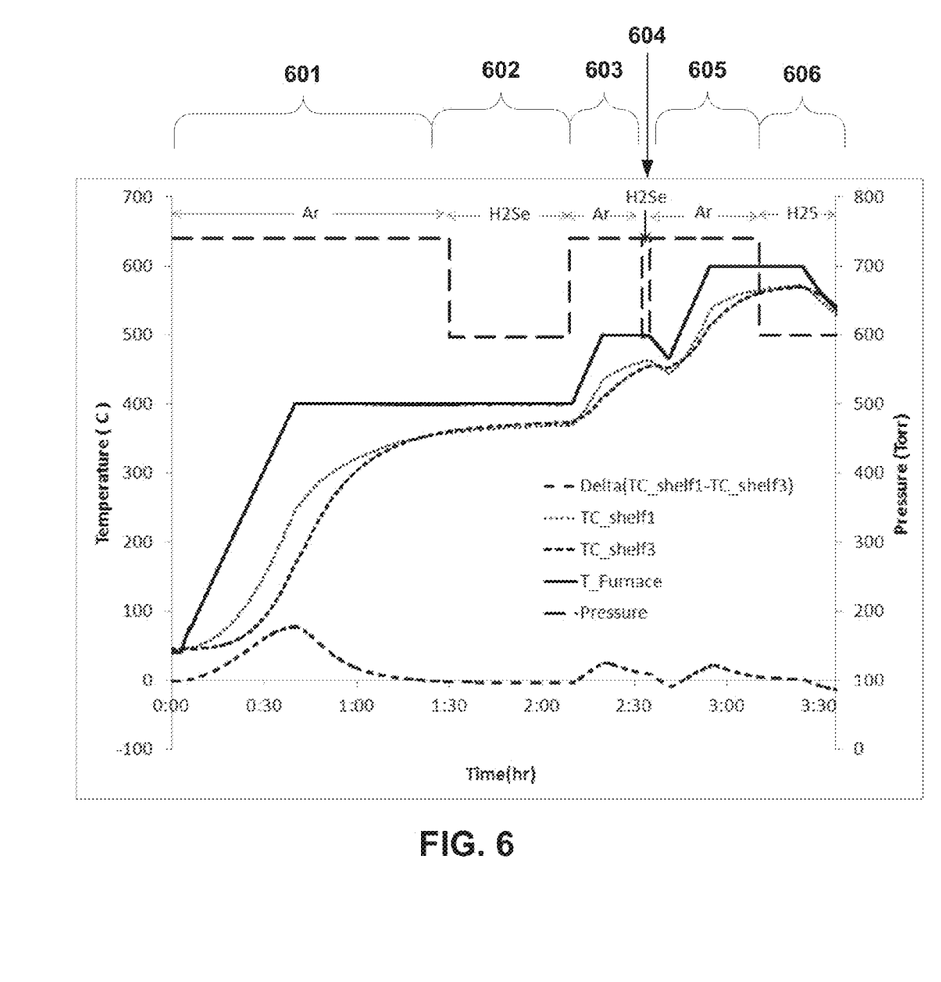
FIG. 6 illustrates a diagram depicting the temperature, temperature uniformity, gas flows, and chamber pressure during a selenization process according to some embodiments of the present invention.

FIG. 6 illustrates a diagram depicting the temperature, temperature uniformity, gas flows, and chamber pressure during a selenization/sulfurization process according to some embodiments of the present invention. The uniformity of the selenization/sulfurization process is largely determined by the temperature uniformity within the furnace. The temperature non-uniformity between the shelves in the furnace is illustrated by the curve labeled "Delta(TC_shelf1-TC_shelf3)". It is noted that the non-uniformity is large during temperature ramp steps from one temperature to the next temperature. If the precursor film is exposed to a source of Se during these periods, the selenization of the film would be non-uniform and the device performance would be poor. This non-uniformity may be addressed by eliminating the exposure to a source of Se during these periods. However, in the absence of an exposure to a source of Se, indium will diffuse and agglomerate at temperatures above about 350 C. In some embodiments of the present invention, the precursor film is exposed to an inert gas flow (i.e. Ar) during the temperature ramp steps, denoted by time period 601 in FIG. 6. To decrease the indium agglomeration, the pressure within the furnace is increased to between about 1 atmosphere and about 2 atmospheres during temperature ramp steps. A pressure of 1 atmosphere has been illustrated in FIG. 6. The target temperature range for time period 601 is between about 350 C and about 450 C, and preferably to between about 400 C and about 450 C.

Once the temperature has stabilized, the pressure in the furnace is reduced to between about 600 Torr and 700 Torr and the precursor film is exposed to a source of Se. In this case, the source of Se is $H_2Se$, denoted by time period 602 in FIG. 6. An exemplary concentration of the $H_2Se$ is about 1 molar % $H_2Se$ in Ar. The temperature uniformity within the furnace is acceptable during this step and the selenization/sulfurization process will also be uniform.

As illustrated in FIG. 6, the furnace is then ramped to an intermediate temperature of between about 450 C and about 550 C, denoted by time period 603 in FIG. 6. As before, during this time, the CIGS film is not exposed to a source of Se. The furnace is filled with an inert gas (i.e. Ar) and the pressure within the furnace is increased to between about 1 atmosphere and about 2 atmospheres during temperature ramp steps. A pressure of 1 atmosphere has been illustrated in FIG. 6.

In some embodiments, it is advantageous to expose the CIGS film to a second selenization/sulfurization process, denoted by time period 604 in FIG. 6. This step completes the selenization/sulfurization of the film. As before, the pressure in the furnace is reduced to about 600 Torr and the precursor film is exposed to a source of Se. In this case, the source of Se is $H_2Se$. The higher temperature results in increased crystallinity, larger grains, and improved optoelectronic performance. To prevent the over-selenization of the film, a fast gas exchange step is introduced near the beginning of the high temperature step. In this process, the $H_2Se$ flow is stopped and the $H_2Se$ gas within the chamber is quickly removed through a combination of an increased inert gas purge and pumping capacity.

As illustrated in FIG. 6, the furnace is then ramped to a final temperature of between about 550 C and about 650 C to anneal the film, denoted by time period 605 in FIG. 6. As before, during this time, the CIGS film is not exposed to a source of Se. The furnace is filled with an inert gas (i.e. Ar) and the pressure within the furnace is increased to between about 1 atmosphere and about 2 atmospheres during temperature ramp steps. A pressure of 1 atmosphere has been illustrated in FIG. 6. The purpose of this anneal step is to allow the indium and gallium to interdiffuse within the film.

In some embodiments, it is advantageous to expose the CIGS film to an optional sulfurization process, denoted by time period 606 in FIG. 6. This step completes the sulfurization of the film. As before, the pressure in the furnace is reduced to about 600 Torr and the precursor film is exposed to a source of S. In this case, the source of S is $H_2S$.

During time periods 602 and 604 discussed above, it is important that the furnace be free of sources of oxygen or water. If oxygen or water is present while the $H_2Se$ is flowing into the furnace, they will react to form elemental Se and/or selenium oxides and will have a negative impact on the selenization of the precursor film. Common sources of oxygen or water are leaks in the seals of the furnace. It is difficult to measure oxygen or water in an $H_2Se$ environment due to the toxicity and corrosive nature of the $H_2Se$. Although oxygen sensors exist, they are costly and may not function due to the corrosive nature of the $H_2Se$ in this application.

Figure 7A:
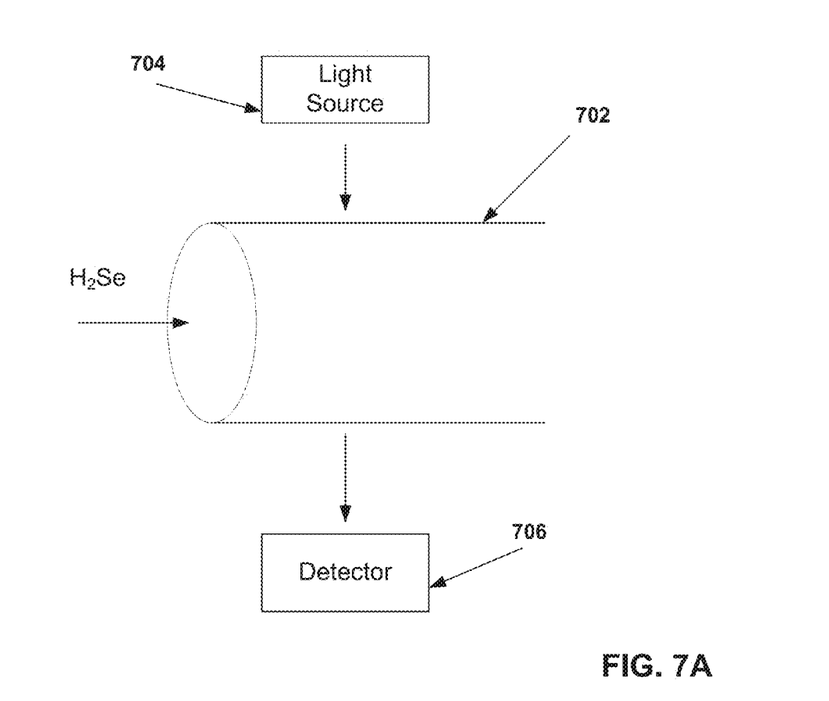
FIGS. 7A and 7B illustrate schematic diagrams of leak detection using transmission.
Figure 7B:
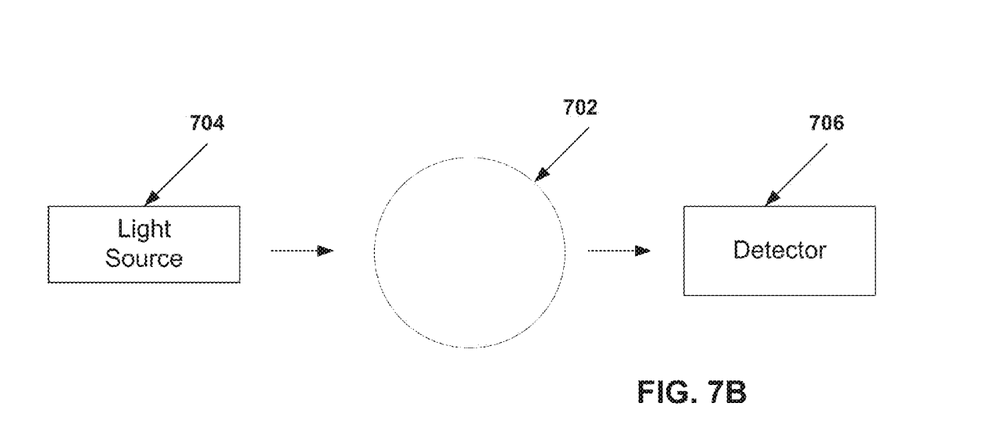

FIGS. 7A and 7B illustrate schematic diagrams of methods of leak detection using transmission. $H_2Se$ reacts with oxygen or water to form selenium compounds that are reddish in color and become opaque as their thickness grows. The reaction is quite efficient and even small amounts of oxygen or water will cause a detectable deposition of the reddish selenium compounds on the walls of the reaction chamber. The deposition of the reddish selenium compounds on the walls of the reaction chamber can be used as part of a method for detecting leaks in a selenization furnace. FIGS. 7A and 7B illustrate a detection method wherein the selenization reaction chamber comprises a transparent quartz tube, 702. A light source, 704, is positioned on one side of the reaction chamber and is incident on the transparent wall of the reaction chamber. Advantageously, the light source is positioned near the entrance of the $H_2Se$ gas source. The light source may be any well known source such as a LED or a laser. Advantageously, the light source emits light with a wavelength between about 400 nm and about 750 nm. The light passes through the reaction chamber and is detected by a detector, 706, positioned opposite the light source. During a selenization process, if a leak occurs in the reaction chamber and oxygen or water is introduced into the reaction chamber, a reddish film of selenium compounds will form on the walls of the reaction chamber as discussed previously. The deposition of this film will cause the intensity of the light incident on the detector to decrease. The decrease in the intensity of the light can be used as an indication of a leak and the processing step can be aborted to prevent damage to the devices being processed. In the case wherein the reaction chamber is opaque, (such as a metal process chamber), transparent surfaces such as windows may be installed in the reaction chamber to allow a transparent light path from the light source, 704, to the detector, 706. In this configuration, the light would be incident upon a first transparent surface (i.e. a first window) and the detector would be located adjacent to a second transparent surface (i.e. a second window) so that the light that is incident upon the detector has passed through both the first transparent surface and the second transparent surface. As discussed previously, the decrease in the intensity of the light can be used as an indication of a leak and the processing step can be aborted to prevent damage to the devices being processed.

Figure 8A:
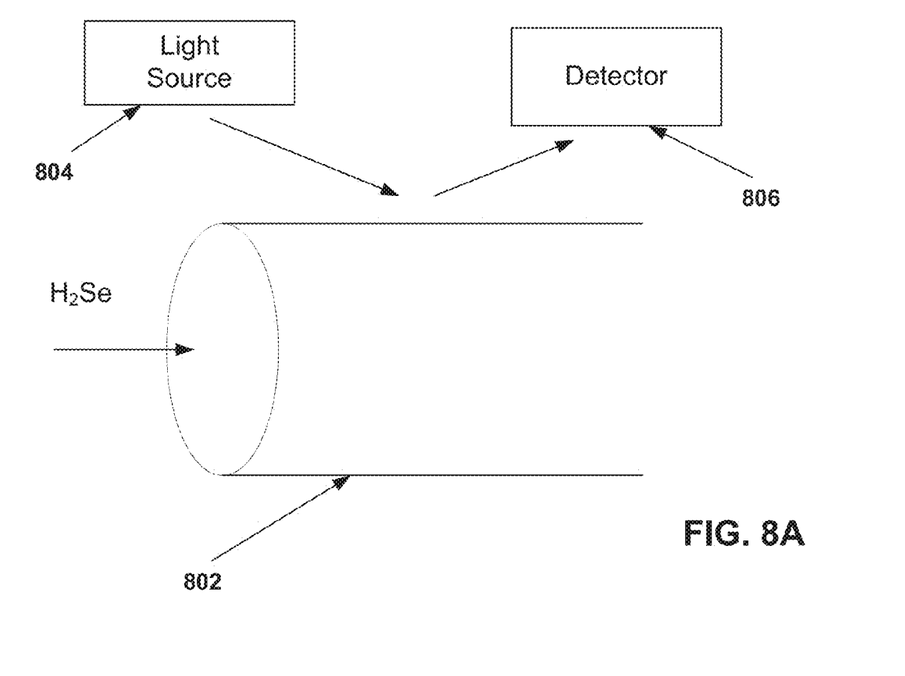
Figure 8B:
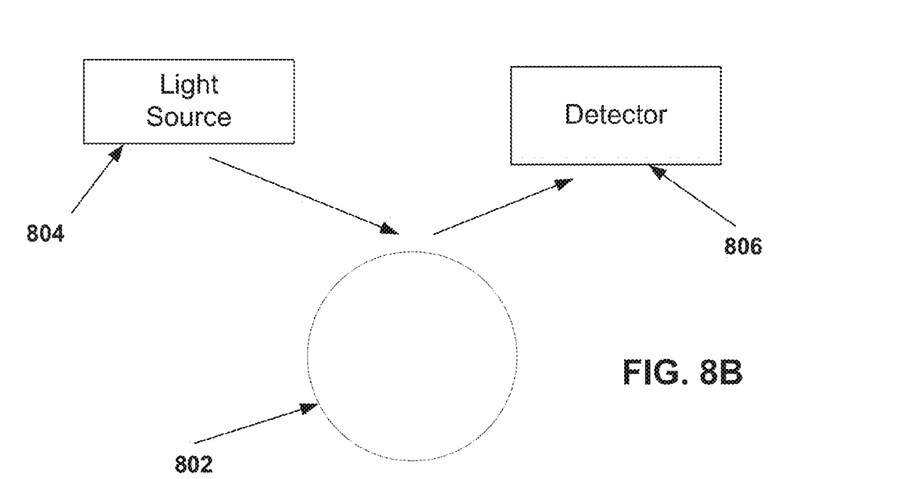

FIGS. 8A and 8B illustrate schematic diagrams of methods of leak detection using reflection. $H_2Se$ reacts with oxygen or water to form selenium compounds that are reddish in color and become opaque as their thickness grows. The reaction is quite efficient and even small amounts of oxygen or water will cause a detectable deposition of the reddish selenium compounds on the was of the reaction chamber. The deposition of the reddish selenium compounds on the was of the reaction chamber can be used as part of a method for detecting leaks in a selenization furnace. FIGS. 8A and 8B illustrate a detection method wherein the selenization reaction chamber comprises a transparent quartz tube, 802. A light source, 804, is positioned on one side of the reaction chamber. Advantageously, the light source is positioned near the entrance of the $H_2Se$ gas source. The light source may be any well known source such as a LED or a laser. Advantageously, the light source emits light with a wavelength in a range of about 400 nm to about 750 nm. In the absence of a leak, the light will be reflected by the walls of the reaction chamber and there will be a first intensity of light incident on a detector, 806, positioned so that the detector captures reflected light from the wall of the reaction chamber. During a selenization process, if a leak occurs in the reaction chamber and oxygen or water is introduced into the reaction chamber, a reddish film of selenium compounds will form on the walls of the reaction chamber as discussed previously. The deposition of this film will cause the light incident on the wall of the reaction chamber to be reflected and captured by the detector, 806. The change in the intensity of the light relative to the first intensity of light can be used as an indication of a leak and the processing step can be aborted to prevent damage to the devices being processed. In the case wherein the reaction chamber is opaque, (such as a metal process chamber), transparent surfaces such as windows may be installed in the reaction chamber to be monitored by the light source, 804, and the detector, 806. In this configuration, the light would be incident upon a first transparent surface (i.e. a window) and the detector would also be located adjacent to the transparent surface so that the light that is incident upon the detector has reflected from the first transparent surface. As discussed previously, a change in the intensity of the light can be used as an indication of a leak and the processing step can be aborted to prevent damage to the devices being processed.

Although the foregoing examples have been described in some detail for purposes of clarity of understanding, the invention is not limited to the details provided. There are many alternative ways of implementing the invention. The disclosed examples are illustrative and not restrictive.

What is claimed:

1. A method for detecting a leak in a reaction chamber during a selenization process comprising:
   positioning a light source adjacent to a first transparent wall of the reaction chamber, wherein light from the light source is incident on the first transparent wall;
   positioning a detector adjacent to a second transparent wall of the reaction chamber, wherein light from the light source is incident on the detector after having passed through the first transparent wall and the second transparent wall reaction chamber;
   flowing $H_2Se$ gas into the reaction chamber; and
   monitoring the intensity of the light incident on the detector, wherein a decrease in light intensity indicates a leak in the seals of the reaction chamber.

2. The method of claim 1 wherein the reaction chamber is a quartz tube.

3. The method of claim 1 wherein the light source is an LED or laser.

4. The method of claim 3 wherein the light source emits light having a wavelength of between about 400 nm and about 750 nm.

5. The method of claim 1 wherein each of the first transparent surface and the second transparent surface of the reaction chamber is a window.

6. The method of claim 1 wherein the light source is an LED or laser.

7. The method of claim 6 wherein the light source emits light having a wavelength of between about 400 nm and about 750 nm.

8. The method of claim 1 wherein the reaction chamber is a quartz tube.

9. The method of claim 1 wherein the light source is an LED or laser.

10. The method of claim 9 wherein the light source emits light having a wavelength of between about 400 nm and about 750 nm.

11. The method of claim 1 wherein the transparent surface of the reaction chamber is a window.

12. The method of claim 1 wherein the light source is an LED or laser.

13. The method of claim 12 wherein the light source emits light having a wavelength of between about 400 nm and about 750 nm.

14. A method for detecting a leak in a reaction chamber during a selenization process comprising:
   positioning a light source adjacent to a first transparent surface of the reaction chamber, wherein light from the light source is incident on the first transparent surface;
   positioning a detector adjacent to a second transparent surface of the reaction chamber, wherein light from the light source is incident on the detector after having passed through the first transparent surface and the second transparent surface of the reaction chamber;
   flowing $H_2Se$ gas into the reaction chamber; and
   monitoring the intensity of the light incident on the detector, wherein a decrease in light intensity indicates a leak in the seals of the reaction chamber.

15. A method for detecting a leak in a reaction chamber during a selenization process comprising:
   positioning a light source adjacent to a transparent wall of the reaction chamber, wherein light from the light source is incident on the transparent wall;
   positioning a detector adjacent to the transparent wall of the reaction chamber, wherein light from the light source is incident on the detector after having reflected from the transparent wall of the reaction chamber;
   flowing $H_2Se$ gas into the reaction chamber; and
   monitoring the intensity of the light incident on the detector, wherein a change in light intensity indicates a leak in the seals of the reaction chamber.

16. A method for detecting a leak in a reaction chamber during a selenization process comprising:
   positioning a light source adjacent to a transparent surface of the reaction chamber, wherein light from the light source is incident on the transparent wall;
   positioning a detector adjacent to the transparent surface of the reaction chamber, wherein light from the light source is incident on the detector after having reflected from the transparent surface of the reaction chamber;
   flowing $H_2Se$ gas into the reaction chamber; and
   monitoring the intensity of the light incident on the detector, wherein a change in light intensity indicates a leak in the seals of the reaction chamber.

\* \* \* \* \*